United States Patent [19]

Asai et al.

[11] Patent Number: 4,681,118

[45] Date of Patent: * Jul. 21, 1987

[54] WATERPROOF ELECTRODE ASSEMBLY WITH TRANSMITTER FOR RECORDING ELECTROCARDIOGRAM

[75] Inventors: Toshio Asai, Uchinadamachi; Yasuhiro Nakaya, Kanazawashi; Yasuaki Onodera, Saitamaken, all of Japan

[73] Assignee: Fukuda Denshi Co., Ltd., Tokyo, Japan

[ * ] Notice: The portion of the term of this patent subsequent to Jan. 20, 2004 has been disclaimed.

[21] Appl. No.: 742,823

[22] Filed: Jun. 10, 1985

[30] Foreign Application Priority Data

Jun. 11, 1984 [JP] Japan ................................. 59-120380

[51] Int. Cl.[4] .............................................. A61B 5/04
[52] U.S. Cl. ..................................... 128/643; 128/903
[58] Field of Search ....................... 128/639, 643, 903

[56] References Cited

U.S. PATENT DOCUMENTS 3,568,663 3/1971 Phipps ................................. 128/643
3,595,218 7/1971 Kirkpatrick ......................... 128/643
4,515,162 5/1985 Yamamoto et al. ................ 128/643

FOREIGN PATENT DOCUMENTS 1466834 3/1969 Fed. Rep. of Germany ...... 128/903

Primary Examiner—Kyle L. Howell
Assistant Examiner—Randy Citrin
Attorney, Agent, or Firm—Pollock, VandeSande & Priddy

[57] ABSTRACT

A waterproof electrode assembly with a transmitter for recording an electrocardiogram, in which the electrodes can reliably be attached on the outer surface of a human body due to bonding force of the adherent sheet and the sucking force caused by returning action of a cup-shaped suction disk to its original shape, the electrodes are not separated from the body even during severe exercise in the water, such as swimming. The waterproofness of the electrode assembly is reliable and durable, and the electrocardiogram of the living body during swimming can be efficiently and accurately recorded, no current leakage phenomenon occurs, the entanglement of the cable with legs and arms can be removed.

1 Claim, 5 Drawing Figures

F I G. 2
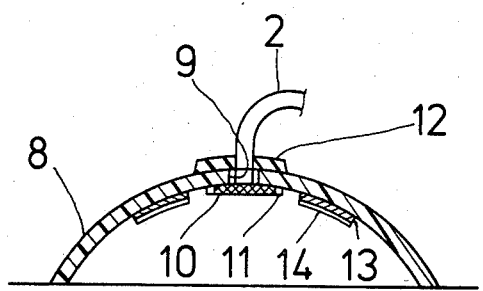
F I G. 3
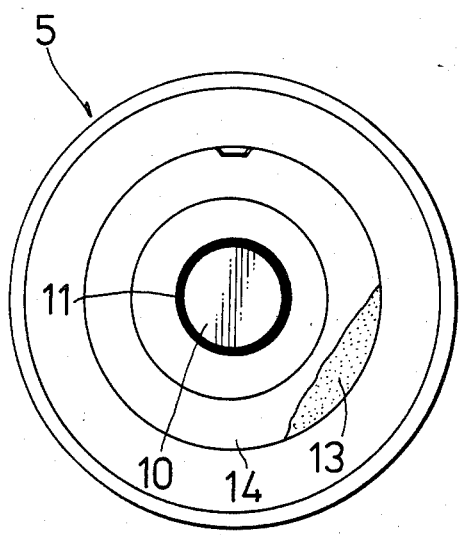

WATERPROOF ELECTRODE ASSEMBLY WITH TRANSMITTER FOR RECORDING ELECTROCARDIOGRAM

FIELD OF THE INVENTION

The present invention relates to a waterproof electrode assembly with a transmitter for recording an electrocardiogram used in inspection on the electrocardiogram to know the function of a heart during exercise in the water, such as swimming or rehabilitation.

BACKGROUND OF THE INVENTION

As a result of recent developments in medical techniques and in the general medical care of hearts, a number of serious and mild cardiac diseases have been discovered and aided by cardiac therapy. However, mild cardiac patients, particularly mild cardiac sick children discovered at school by cardiac examinations conducted nationwide, have been prevented from swimming as being too severe an exercise.

In conventional infant circulatory organ science, the reason that the mild cardiac infant cannot swim safely is the result of consideration of the energy consumption and the result of inspection of an electrocardiogram of the infants on the ground. So far, there has been no electrode for recording the electrocardiogram during swimming. Therefore, the swimming restrictions are not based on results of the inspection of an electrocardiogram recorded during actual swimming.

However, the circulatory action during swimming is different from that during exercises on the ground, and abnormal variations are observed during swimming. On the other hand, at present, since accurate circulatory action of a pupil during swimming is unknown, the safety of the mild cardiac sick pupil during swimming cannot be confirmed. It is difficult to give approval for swimming to the mild cardiac sick pupil based on a conventional inspection. Consequently, it becomes necessary to prove that the pupil can swim safely by recording an electrocardiogram during actual swimming.

In order to record the electrocardiogram of the living body during swimming, it is necessary to detect ultrafine currents induced on the skin of the living body during swimming by electrodes bonded on the skin, to lead it to an electrocardiograph on the ground and to measure the variation in the potential generated in a living body by the electrocardiograph.

Since the electrodes bonded on the skin of the living body are easily separated from the skin in the water, the electrodes may be bonded with adhesive or bonding agent on the skin in some cases. However, it is troublesome to bond the electrodes on the skin and it gives a load for an examinee. Even if the electrodes are bonded with adhesive on the skin, they can be separated from the skin during severe swimming exercise. Further, since the waterproofness of the electrodes may not be adequate, there is a drawback that a good electrocardiogram of the living body during swimming cannot be obtained.

In order to record the electrocardiogram of the living body during swimming, it is necessary to put the electrode on the skin surface of the living body and to connect each of the electrodes through respective cables to an electrocardiograph placed on the ground.

In case that the electrocardiogram of the living body during swimming is recorded by the electrocardiograph placed on the ground as described above, when the living body swims for a long distance, the cable must be lengthened in response to the swimming distance. As the cable becomes longer, the cost increases, and it arises that an accurate electrocardiogram cannot be obtained due to leakage phenomenon of the ultrafine current.

SUMMARY OF THE INVENTION

It is a primary object of the present invention to provide a waterproof electrode assembly with a transmitter for recording an electrocardiogram, in which the electrodes are not easily separated from the body during swimming, are attached easily, and can accurately record the electrocardiogram of swimming body.

According to the present invention, there is provided a waterproof electrode assembly with a transmitter for recording an electrocardiogram, in which each electrode comprises a cup-shaped suction disc made of a waterproof elastic material which has a through hole at the center thereof, an electrode plate which is hermetically provided on the concave surface side of said suction disc to close said through hole, a lead wire which has one end inserted from the convex surface side to the concave surface of said sucking disc through said through hole and connected to said electrode plate, elastic sealing members for hermetically sealing the contacting portion between the outer peripheral edge portion of said electrode plate and the concave surface of said suction disc and the gap between the periphery of said wire and the convex surface of the suction disc respectively, an annular body surface adherent sheet which is bonded on the concave surface of the suction disc to surround said electrode plate, and a wireless transmitter connected to said electrodes.

BRIEF DESCRIPTION OF THE DRAWINGS

The present invention and its operation will be described in detail in the embodiments shown in the accompanying drawings.

FIG. 2 is a longitudinal sectional view of the electrodes of FIG. 1;

FIG. 3 is a plan view of the electrode of FIG. 2;

DETAILED DESCRIPTION OF THE INVENTION

Figure 1:
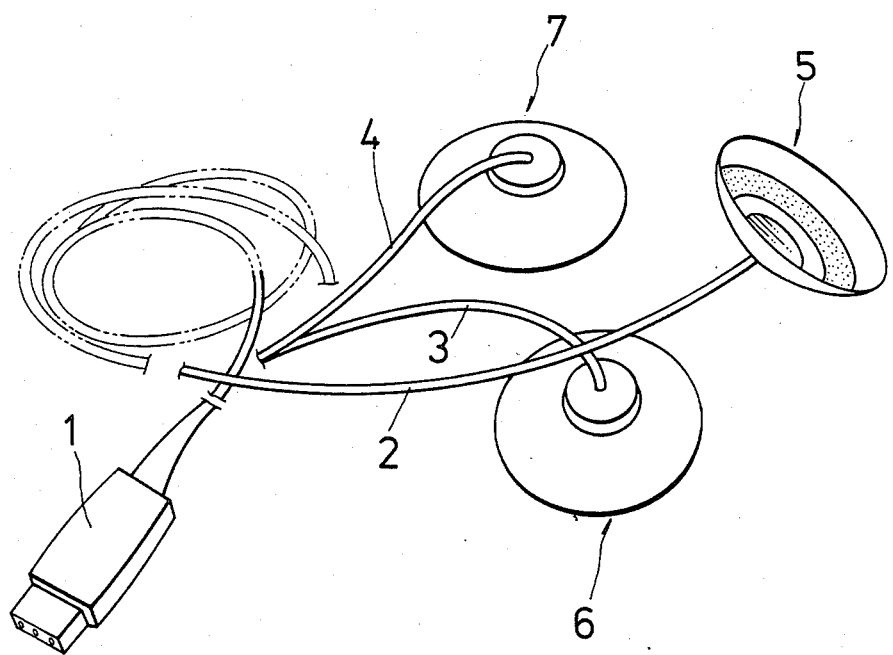
FIG. 1 is a perspective view showing an embodiment in which a combination of electrodes and lead wires are not connected to the transmitter.

FIG. 1 is a perspective view showing an embodiment having a combination of electrodes and lead wires according to the present invention. In FIG. 1, reference numeral 1 designates a connector, three lead wires 2, 3, 4 are connected to one end of the connector 1, and electrodes 5, 6, 7 are respectively connected to one end of the three lead wires 2, 3, 4, respectively.

Since the construction of the electrodes 5, 6, 7 are identical, the construction of only electrode 5 will be described with reference to FIGS. 2 and 3. The electrode 5 has a cup-shaped suction disc made of waterproof synthetic resin elastic material. A through hole 9 is formed at the center of the suction disc 8, and one end of the lead wire 2 is inserted from the convex side of the suction disc 8 into the hole 9 toward the concave side.

An electrode plate 10 is connected to one end of the lead wire 2 and placed to close the hole 9 on the concave side of the disc 8.

A contacting portion of the plate 10 between the outer periphery portion of the plate 10 and the concave surface of the suction disc 8 is hermetically sealed by an elastic sealing material 11 such as silicone rubber. A gap between the periphery of the lead wire 2 and the convex surface of the suction disc 8 is hermetically sealed by an elastic sealing material 12 such as a silicone rubber, thereby preventing immersion in water from the outer surface of the suction disc 8. An annular body surface adherent sheet 14 is bonded with bonding agent 13 along the concentric circle surrounding the plate 10 on the concave surface of the suction disc 8, and adhesive is coated also on the surface of the adherent sheet 14.

Further, a transmitter 15 for transmitting an electrocardiac signal detected by the plate 10 to a remotely placed receiver 18 (FIG. 5) is provided at the other end of the connector 1, to which the other ends of the wires 2, 3, 4 are connected.

Figure 4:
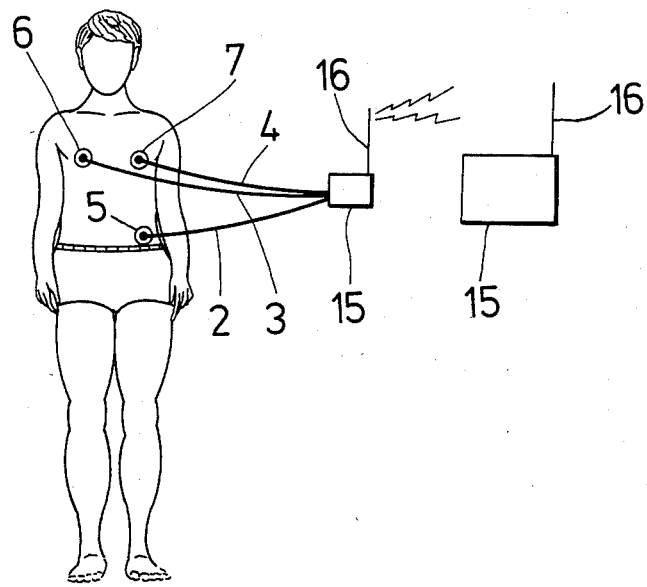
FIG. 4 is a view of the electrodes with a transmitter.
Figure 5:
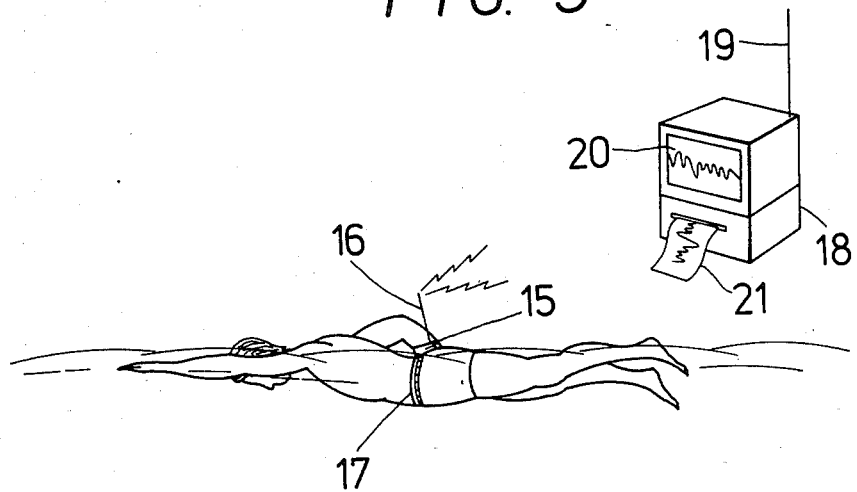
FIG. 5 is a view showing an electrocardiogram which recorded on the basis of the electrocardiac signal received remotely.

In recording the electrocardiogram, waterproof electrodes 5, 6, 7 are put on suitable positions of the skin surface of a body as shown in FIG. 4, and the transmitter is put on the body with a transmitter mounting band 17 as shown in FIG. 5. Upon pressing the suction disc 8, the adherent sheet 14 which is bonded on the concave surface of the suction disc 8 sticks on the skin of the body, and a force acts on the suction disc 8; thus the electrodes 5, 6, 7 are put on the skin surface of the body so that they are not separated from the body even during severe exercise in the water, such as swimming.

Letting the living body swim as shown in FIG. 5 after putting the electrode assembly with transmitter on the body, an electrocardiac signal of the living body during swimming is detected by the electrode plate 10, and led through the wires 2, 3, 4 to the transmitter 15.

The electrocardiac signal led to the transmitter 15 is transmitted from an antenna 16, the transmitted signal is received by an antenna 19 of a receiver 18 placed on the ground. The received signal is indicated on a CRT 20, or recorded as an electrocardiogram on a recording sheet 21.

According to the present invention, since the electrodes comprise the cup-shaped suction disc and the body surface adherent sheet which is bonded on the concave surface of the cup-shaped suction disc, the electrodes can reliably be attached on the outer surface of the human body due to the bonding force of the adherent sheet and the suction force caused by returning action of the suction disc to its original shape, so that the electrodes are not separated from the body even during severe exercise in the water, such as swimming.

Since the electrodes comprise the cup-shaped suction disc, the electrodes are attached on the outer surface of the body merely by pressing the suction disc against the outer surface of the body. Thus, excessive labor such as bonding the electrodes with adhesive on the body can be eliminated, and the electrodes can be easily bonded without the load for the examinee.

Further, the cup-shaped suction disc is made of waterproof elastic material, and the contacting portion between the outer peripheral edge portion of the electrode plate and the concave surface of the disc, and the gap between the peripheral surface of the lead wires and the convex surface of the disc are hermetically sealed by the elastic seals. Thus, the electrodes according to the present invention have the advantages that their waterproofness is reliable and durable.

In addition, since the wireless transmitter 15 for transmitting a cardiac signal detected by the electrode plate 10 to a remotely placed receiver is connected to the other ends of the lead wires, a cable for connecting the electrodes and the electrocardiograph can be eliminated. As a result, there are various advantages such that the electrocardiogram of the living body during swimming can be efficiently recorded, no current leakage phenomenon occurs, the electrocardiogram can be accurately recorded, and entanglement of the cable with legs and arms is avoided.

While the present invention has been described in detail with respect to a certain preferred embodiment of the invention, it will be understood by those skilled in the art that various changes and modifications may be made without departing from the spirit and scope of the invention, and it is intended therefore to cover all such changes and modifications in the appended claims.

What is claimed is:

1. Apparatus for recording an electrocardiogram comprising a waterproof electrode assembly, said electrode assembly having a plurality of electrodes, and each of said electrodes comprising:
   (a) a cup-shaped suction disc constructed from a waterproof, elastic material, said disc having a concave side, a convex side and a through-hole at the center thereof;
   (b) an electrode plate having an outer peripheral edge hermetically sealed to the concave surface of said suction disc and closing said through-hole;
   (c) a lead wire extending from said electrode plate past the convex surface of said suction disc;
   (d) elastic sealing means for hermetically sealing together the outer peripheral edge of said electrode plate and the portions of the concave surface of said suction disc in contact with said peripheral edge of said electrode plate;
   (e) elastic sealing means hermetically sealing the lead wire at the convex surface of the suction disc;
   (f) an annular, body-surface adherent strip surrounding said electrode plate and bonded to the concave surface of the suction disc; and
   (g) a wireless transmitter connected to said electrode.

* * * * *